(12) United States Patent
Lauchner

(10) Patent No.: US 9,597,137 B2
(45) Date of Patent: Mar. 21, 2017

(54) CATHETER WITH INTEGRATED CEMENT DELIVERY BALLOON

(71) Applicant: Kyphon SÀRL, Neuchâtel (CH)

(72) Inventor: Craig E. Lauchner, Mountain View, CA (US)

(73) Assignee: Kyphon SÀRL, Neuchâtel (CH)

( * ) Notice: Subject to any disclaimer, the term of this patent is extended or adjusted under 35 U.S.C. 154(b) by 0 days.

(21) Appl. No.: 15/191,994

(22) Filed: Jun. 24, 2016

(65) Prior Publication Data

US 2016/0302836 A1    Oct. 20, 2016

Related U.S. Application Data

(62) Division of application No. 13/735,671, filed on Jan. 7, 2013, now Pat. No. 9,387,030.

(51) Int. Cl.
| | |
|---|---|
| *A61B 17/58* | (2006.01) |
| *A61B 17/60* | (2006.01) |
| *A61F 2/00* | (2006.01) |
| *A61B 17/88* | (2006.01) |
| *A61B 17/00* | (2006.01) |

(52) U.S. Cl.
CPC ...... *A61B 17/8811* (2013.01); *A61B 17/8855* (2013.01); *A61B 2017/00951* (2013.01)

(58) Field of Classification Search
CPC ............ A61B 17/8802; A61B 17/8805; A61B 17/8811; A61B 17/8819; A61B 17/885; A61B 17/8852; A61B 17/8855; A61B 17/8858
USPC ...................................................... 606/92–94
See application file for complete search history.

(56) References Cited

U.S. PATENT DOCUMENTS

| | | | |
|---|---|---|---|
| 6,248,110 B1 | 6/2001 | Reiley et al. | |
| 7,666,205 B2* | 2/2010 | Weikel | A61B 17/025 606/192 |
| 7,811,290 B2 | 10/2010 | Rabiner | |
| 2006/0009779 A1 | 1/2006 | Collins et al. | |
| 2008/0249603 A1* | 10/2008 | Schwardt | A61B 17/8811 606/192 |
| 2009/0105711 A1* | 4/2009 | Mitchell | A61B 17/1757 606/92 |

* cited by examiner

*Primary Examiner* — Si Ming Ku

(57) ABSTRACT

A bone filling device includes a catheter that defines a longitudinal axis and extends between a proximal end and a distal end. A first lumen extends along the longitudinal axis of the catheter and defines a first passageway. A second lumen extends along the longitudinal axis of the catheter and defines a second passageway. An inflatable body includes a wall that defines a fillable cavity. The fillable cavity is in fluid communication with the first passageway. A bone filler delivery port continuous with the second passageway and configured to dispense bone filling material.

15 Claims, 5 Drawing Sheets

CATHETER WITH INTEGRATED CEMENT DELIVERY BALLOON

CROSS REFERENCE TO RELATED APPLICATIONS

This application is a divisional application of U.S. patent application Ser. No. 13/735,671, filed Jan. 7, 2013, which is incorporated by reference herein, in its entirety.

TECHNICAL FIELD

The present disclosure generally relates to medical devices for the treatment of musculoskeletal structures, and more particularly to a surgical system and method employing a cement delivery system and an inflatable balloon.

BACKGROUND

Extremity fractures of a calcaneus or other bone may be reduced percutaneously using Inflatable Bone Tamps (IBTs). While effective, IBTs are typically designed for the spine and the lifting of vertebral bodies. The inflation profiles of these balloons are most effective at lifting flat surfaces. However, calcaneus fractures typically occur on the superior, anterior portion of the bone, which normally has an angled orientation. A single IBT is typically not sufficient to reorient the surface satisfactorily. Many times, multiple balloons are required to return the calcaneus surface to a proper orientation. This disclosure describes an improvement over these prior art technologies.

Bone filling material is often used with IBTs, however the IBTs would need to be deflated and removed before bone filling material such as bone cement can be deployed. With the removal of the IBT, often height restoration is lost. Thus, what is needed is a device that would allow bone cement delivery while maintaining height restoration.

SUMMARY

Accordingly, a bone filling device includes a catheter that defines a longitudinal axis and extends between a proximal end and a distal end. A first lumen extends along the longitudinal axis of the catheter and defines a first passageway. A second lumen extends along the longitudinal axis of the catheter and defines a second passageway. An inflatable body includes a wall that defines a fillable cavity. The fillable cavity is in fluid communication with the first passageway. A bone filler delivery port continuous with the second passageway and configured to dispense bone filling material. The device is configured for insertion through a cannula into tissue.

A method of filling bone comprising inserting a cannula into bone. Inserting a catheter into the cannula. The catheter defines a longitudinal axis and extends between a proximal end and a distal end and includes a first lumen extending along the longitudinal axis of the catheter and defines a first passageway. A second lumen extending along the longitudinal axis of the catheter and defines a second passageway. An inflatable body having a wall that defines a fillable cavity. The fillable cavity is in fluid communication with the first passageway. A bone filler delivery port continuous with the second passageway and configured to dispense bone filling material. Inflating the balloon such that the balloon applies a force capable of compacting cancellous bone and moving fractured bone. Inserting a bone filler delivery port through the passageway and delivering a bolus of bone filler material while the balloon is inflated. Removing the bone filler delivery port. Allowing for the bone filler material to cure such it forms a shell of bone filler material at the distal end of the balloon and is capable of maintaining a restored height to the bone and deflating and removing the balloon.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
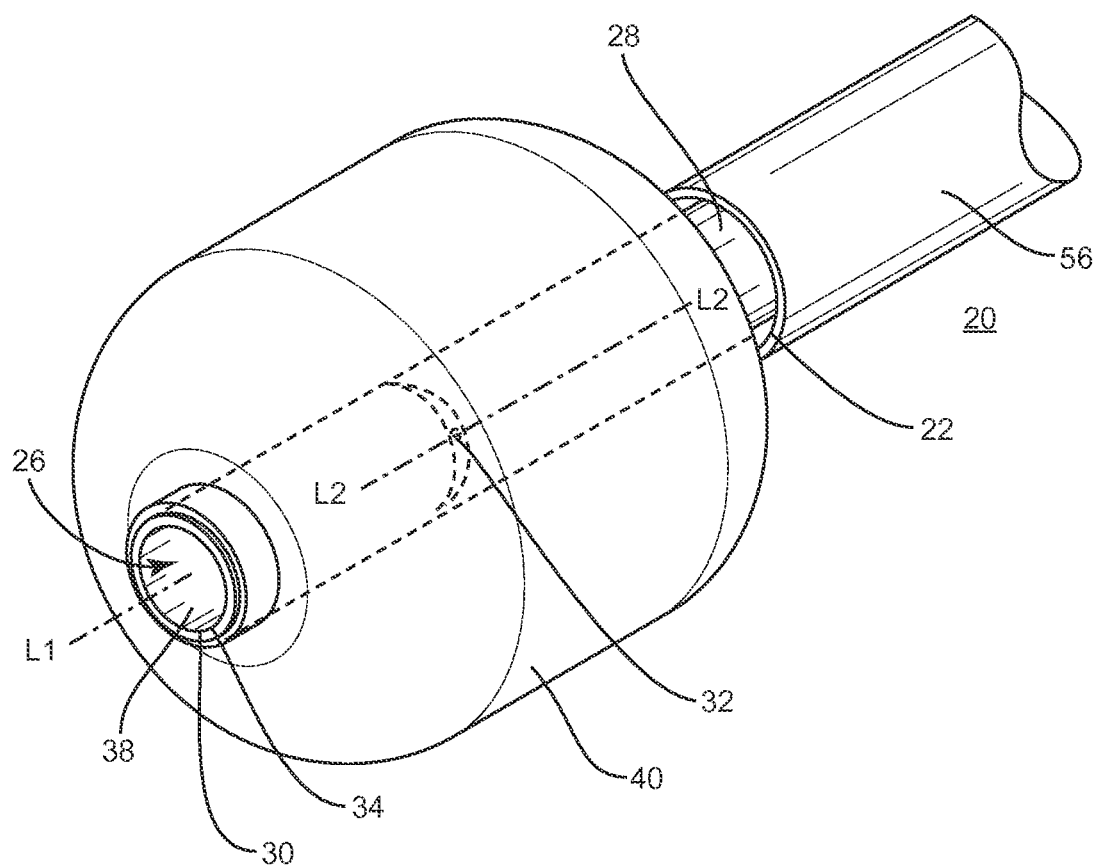
FIG. 1 is a perspective view of one embodiment of components of a catheter system in accordance with the principles of the present disclosure.

The exemplary embodiments of the surgical system and related methods of use disclosed are discussed in terms of medical devices for the treatment of musculoskeletal disorders and more particularly, in terms of a surgical system and method for bone repair. It is envisioned that the surgical system and method may be employed in applications such as for correction of fractures, depressions and breaks. For example, the surgical system and method can include inflatable bone tamps (IBT) presenting an angled surface for the repair of bones.

In one embodiment, the system and method include an inflatable bone tamp that reduces the complexity of a procedure where a surface for a bone repair needs an angled or curve IBT profile. The IBT has an angled surface provided by employing a series of balloons, which form a composite shape. The balloons may be formed from a compliant material to aid in removing the IBT after use. The composite shape of the IBT provides a sufficient volume to reduce depressions or displaced bone tissues, which is less than conventional IBTs.

In kyphoplasty procedures surgeons find current devices lack the ability to maintain vertebral body height restoration achieved by the balloon once the balloon is deflated and removed to insert a bone cement delivery device. In one embodiment, a catheter is provided that integrates an inflatable balloon and a cement delivery device within the single catheter. The balloon is inflated to restore height to the bone. Once height restoration is achieved, a bone filling device is inserted and a small cement bolus is deployed at the distal end of the catheter while the balloon remains inflated. The cement cures and forms an egg shell-like structure around at least the front portion of the balloon which us sufficient to maintain the restored height. Once the cement cures enough to stabilize the height, the cement delivery device and the balloon are removed. The cavity can then be back filled with additional bone cement as needed.

The cross section of the balloon catheter maximizes for cement delivery and minimizes for saline or contrast delivery. To manufacture the device, approximately a centimeter of the catheter is trimmed to expose the lumen inside the balloon. An adhesive, such as, for example, a UV-curing cement is used to adhere the balloon to the catheter. In one embodiment, marker bands are provided on the catheter and/or balloon so as to help in determining the orientation of the device in situ.

The device of the present disclosure can be utilized for extremities use, for filling metastatic lesions as well as other medical procedures.

It is contemplated that one or all of the components of the surgical system may be disposable, peel-pack, pre-packed sterile devices. One or all of the components of the surgical system may be reusable. The surgical system may be configured as a kit with multiple sized and configured components.

It is envisioned that the present disclosure may be employed to treat bones, and in particular extremity bones such as the calcaneus. It should be understood that the present principles are applicable to any bone structures, including but not limited to bones of the spine, legs, feet, arms, etc. It is contemplated that the present disclosure may be employed with other osteal and bone related applications, including those associated with diagnostics and therapeutics. It is further contemplated that the disclosed surgical system and methods may alternatively be employed in a surgical treatment with a patient in a prone or supine position, and/or employ various surgical approaches, including anterior, posterior, posterior mid-line, direct lateral, postero-lateral, antero-lateral, etc. approaches in the calcaneus, spine or other body regions. The present disclosure may also be alternatively employed with procedures for treating the muscles, ligaments, tendons or any other body part. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-7, there are illustrated components of a surgical system, such as, for example, a catheter system 20 and embodiments in accordance with the principles of the present disclosure.

The components of catheter system 20 can be fabricated from biologically acceptable materials suitable for medical applications, including metals, synthetic polymers, ceramics and bone material and/or their composites, depending on the particular application and/or preference of a medical practitioner. For example, the components of catheter system 20, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TOP, calcium sulfate, or other resorbable polymers such as polyaetide, polyglycolide, polytyrosine carbonate, polycaroplaetohe and their combinations. Various components of catheter system 20 may have material composites, including the above materials, to achieve various desired characteristics such as strength, rigidity, elasticity, compliance, biomechanical performance, durability and radiolucency or imaging preference. The components of catheter system 20, individually or collectively, may also be fabricated from a heterogeneous material such as a combination of two or more of the above-described materials. The components of catheter system 20 may be monolithically formed, integrally connected or include fastening elements and/or instruments, as described herein.

Catheter system 20 is employed, for example, with an open, mini-open or minimally invasive surgical technique to attach move or apply pressure to a bone fragment, fracture or surface, such as, in treating calcaneus fractures. As shown in FIG. 1, system 20 includes a catheter 22 extending between a proximal end 24 and a distal end 26. Catheter 22 defines a longitudinal axis L1. Catheter 22 includes an outer surface 28 and an inner surface 30. It is contemplated that surfaces 28, 30 may have surface configurations such as, for example, smooth, rough, arcuate, undulating, dimpled and/or textured, according to the requirements of a particular application.

Figure 2:
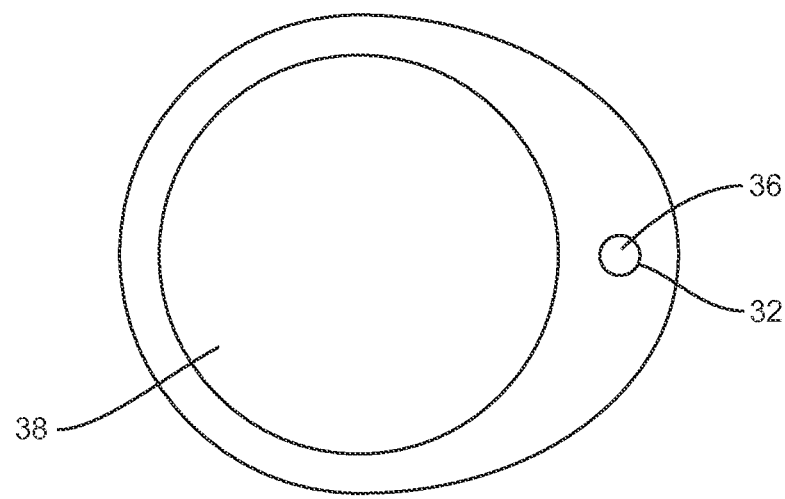
FIG. 2 is a plan view of components of the system of FIG. 1 in accordance with the principles of the present disclosure.
Figure 3:
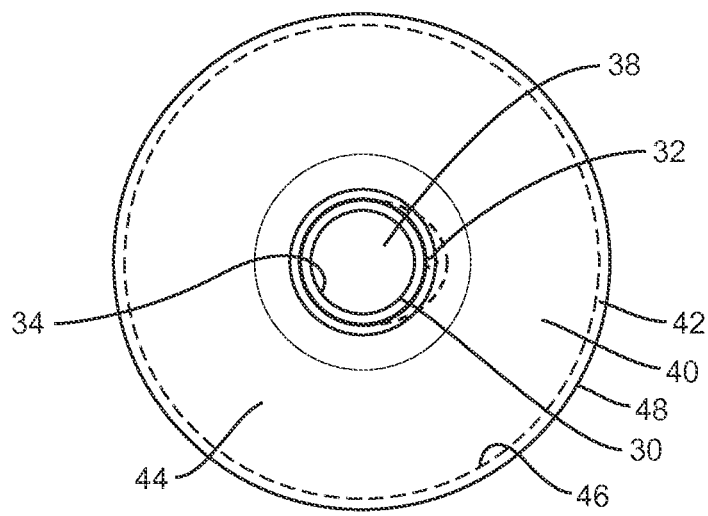
FIG. 3 is a plan view of components of the system of FIG. 1 in accordance with the principles of the present disclosure.
Figure 4:
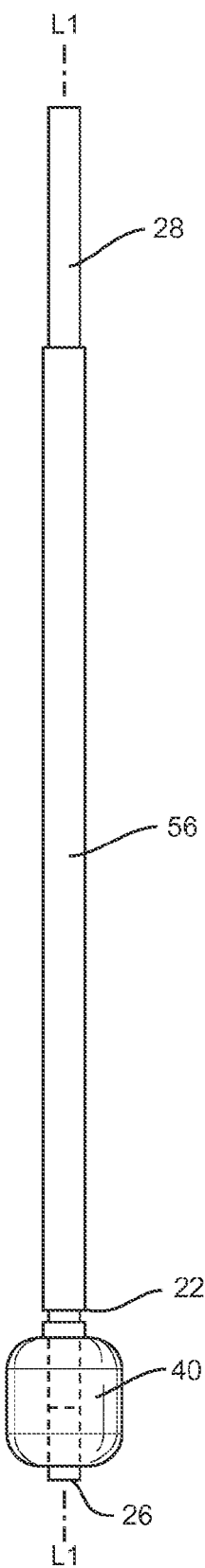
FIG. 4 is a side view of components of the system of FIG. 1 in accordance with the principles of the present disclosure.
Figure 5:
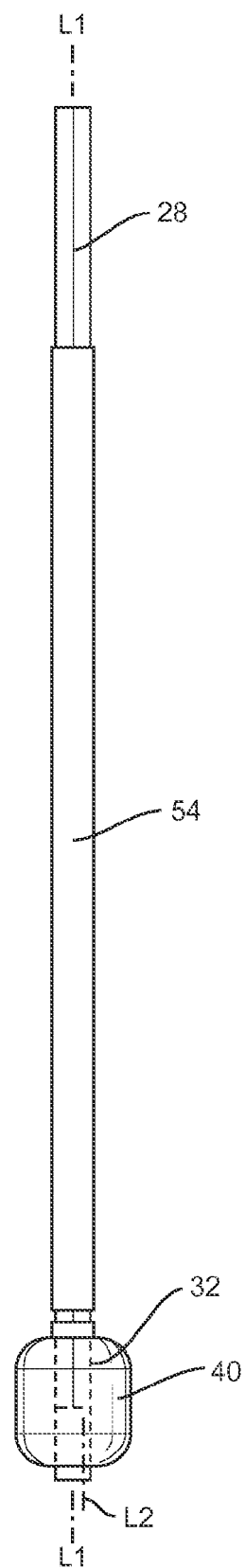
FIG. 5 is a top view of components of the system of FIG. 1 in accordance with the principles of the present disclosure.
Figure 6:
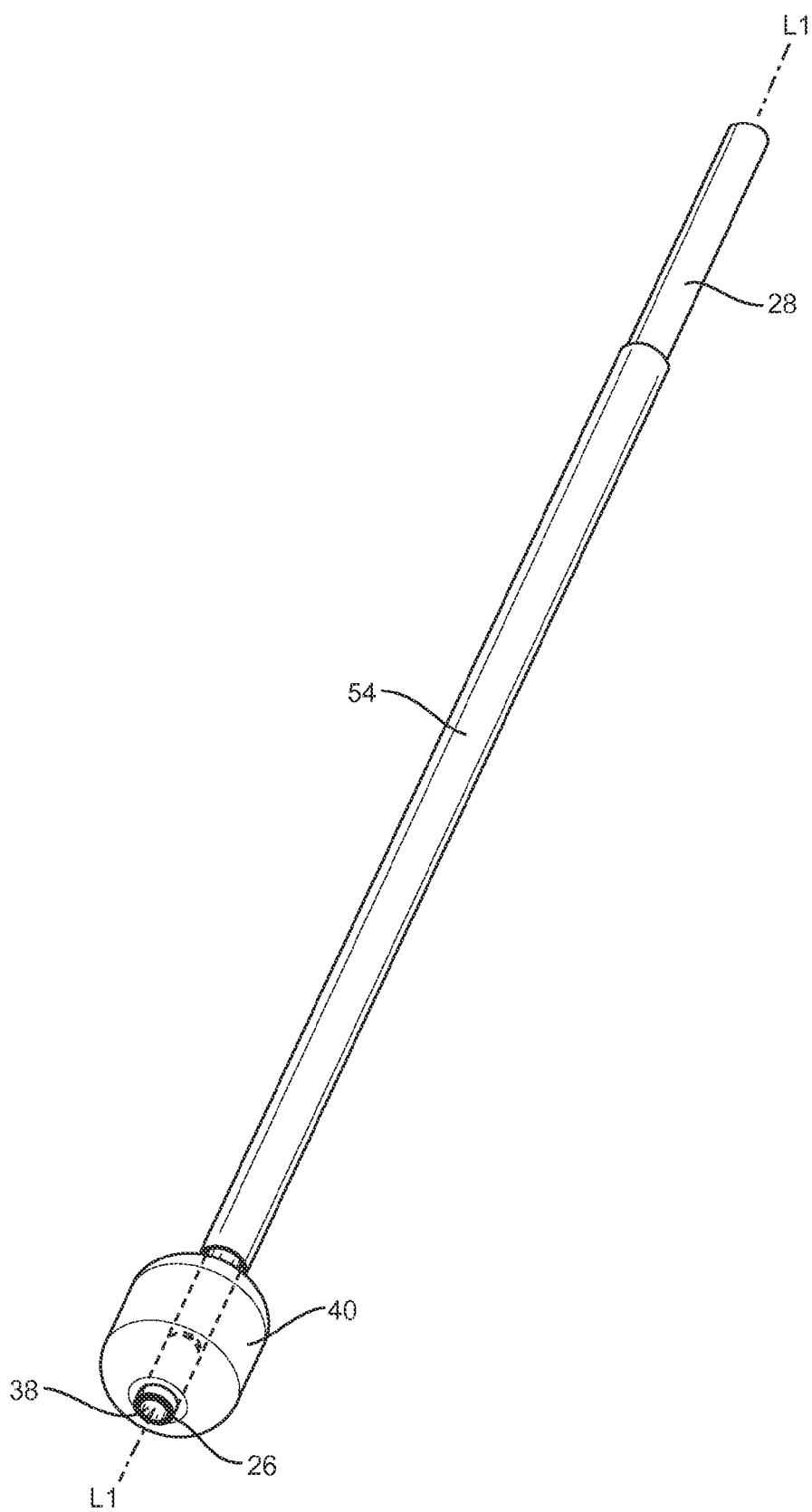
FIG. 6 is a side perspective view of components of the system of FIG. 1 in accordance with the principles of the present disclosure.

As shown in FIGS. 1-2, Catheter 22 includes a first lumen 32 and a second lumen 34. Lumen 32 is disposed along outer surface 28. Lumen 32 defines a first passageway 36 defining longitudinal axis L2 that extends parallel to axis L1. It is contemplated that passageway 36 can extend along axis L1, perpendicular to axis L1 or transverse to axis L1. Lumen 32 is configured to inflate or deflate an inflatable body, discussed herein. Lumen 34 is disposed along inner surface 30 and defines a second passageway 38. Passageway 38 extends along axis L1. It is contemplated that passageway 36 can extend parallel to axis L1, perpendicular to axis L1 or transverse to axis L1. Lumen 34 is configured to receive a bone filling device, such as, for example, a bone filling tube, as discussed herein.

System 20 includes an inflatable body, such as, for example, a balloon 40. Balloon 40 includes a wall 42 configured to define a fillable cavity 44. Wall 42 includes an inner surface 46 and an outer surface 48. Inner surface 46 forms cavity 44. Outer surface 48 is configured to engage and apply force to tissue, such as, for example, cancellous bone in a traumatized calcaneus bone. It is contemplated that surface 48 may have surface configurations to enhance engagement such as, for example, smooth, rough, arcuate, undulating, dimpled and/or textured, according to the requirements of a particular application. It is envisioned that all or only a portion of balloon 40 may have cross section configurations, such as, for example, oval, oblong, triangular, square, polygonal, irregular, uniform, non-uniform, offset, staggered, and/or tapered depending on a particular application. Balloon 20 is in configured to be in communication with lumen 32 such that passageway 36 receives material to inflate and/or deflate balloon 40.

System 20 includes a material delivery port, such as, for example, a bone filler delivery port 50 located at distal end 26. It is contemplated that other materials such as, saline, contrast or water can be deployed through port 50 in addition to or instead of the bone filling material. Port 50 is continuous with the passageway 38 and configured to dispense bone filling material. In one embodiment, port 50 is configured to receive a bone filler tube (not shown). The bone filler tube is inserted into passageway 38 such that an end of the bone filler tube extends out of port 50 and past distal end 26. In this configuration, the bone filer tube dispenses bone filling material 54 into a cavity C. In another embodiment, bone filling material 54 is dispensed through passageway 38 and out port 50 such that an actuating mechanism, such as, for example, a syringe (not shown) is utilized to push bone filling material 54 through passageway, out distal end 26 and into cavity C. A bolus of bone filler material 54 is deployed from port 50 such that material 54 spreads over a portion of outer surface 48 of balloon 40 or directly forward balloon 40 such that the bone filler material 54 forms an eggshell-like shape around surface 48 or forward to the surface. When material 54 cures and hardens, balloon 40 can be deflated. The eggshell-like structure is configured to maintain the height between the collapsed bone structures such that additional material 54 can be injected. The initial bolus of cement forming the eggshell-like structure that maintains the height as the balloon is deflated and removed, blends with the additional cement added so as to create a continuous cement structure filling the void created by the balloon. It is important to deliver the additional cement while the eggshell-like structure is still hardening so that the additional cement hardens so as to be continuous with the cement forming the eggshell-like structure.

System 20 further includes a cannula 56. Catheter 22 is configured for insertion through cannula 56 and into tissue such that balloon 40 can be inflated and apply a force F capable of compacting cancellous bone and moving fractured bone to restore height to the bone.

In assembly, operation and use, system 20 is employed with a surgical procedure, such as, for a correction or treatment of bone fractures. It is contemplated that one or all of the components of system 20 can be delivered or implanted as a pre-assembled device or can be assembled in situ.

For example, as shown in FIGS. 1-7, system 20, described above, can be employed with a surgical correction treatment of an applicable condition or injury of an affected portion of a, calcaneus bone, bones of the feet or hands, bones of the spine, bones of the arms and legs, etc. and other areas within a body.

In use, to treat a fracture, a medical practitioner obtains access to a surgical site including the fractured bone in any appropriate manner, such as through incision and retraction of tissues. In one embodiment, a drill is employed to remove bone tissue to provide access to a repair site. It is envisioned that system 20 can be used in any existing surgical method or technique including open surgery, mini-open surgery, minimally invasive surgery and percutaneous surgical implantation, whereby the fractured or injured bone is accessed through a mini-incision or sleeve that provides a protected passageway to the area. Once access to the surgical site is obtained, the particular surgical procedure can be performed for treating the injury or disorder. The configuration and dimension of system 20 is determined according to the configuration, dimension and location of a selected section of the bone fracture and the requirements of a particular application.

An incision is made in the body of a patient and a cutting instrument (not shown) creates a surgical pathway for implantation of components of system 20. This may include the use of a cannula or other device. A preparation instrument (not shown) can be employed to prepare tissue surfaces, as well as for aspiration and irrigation of a surgical region according to the requirements of a particular surgical application.

Figure 7:
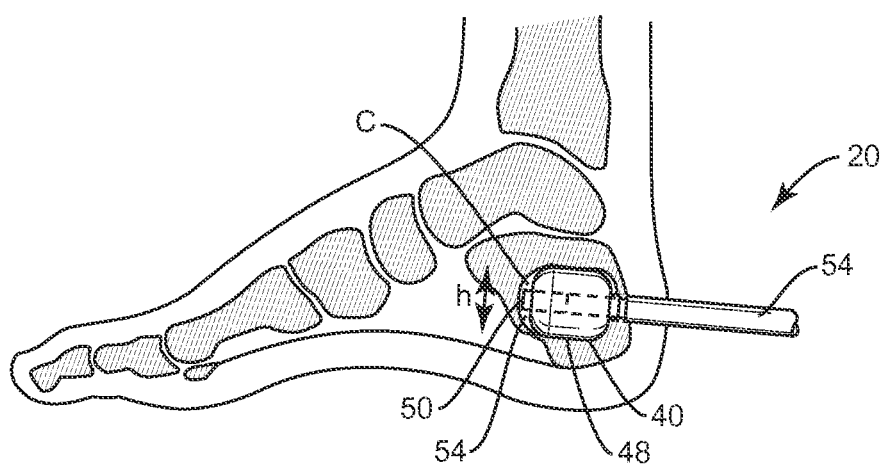
FIG. 7 is a side view of components of the system of FIG. 1 disposed with calcaneus bone in a heel.

Cannula 56 is inserted into the surgical pathway into cavity C located between fractured bones in a heel, as shown in FIG. 7. It is contemplated that system 20 can be utilized with other areas of bone fractures such as vertebral, tibia or hip. Catheter system 20 is inserted through cannula 56. Balloon 40 is inflated by lumen 32 such that balloon expands into cavity C and wall 42 exerts a force F on the cancellous to restore the height h of the fractured bone, as shown in FIG. 7. When a desired height h is restored to the fractured bone, bone filling material 54 is inserted through passageway 38, either via a tube or a syringe, into port 50, either via a bone filling device or use of a syringe, while the balloon is still inflated. A bolus of bone filler material 54 is deployed from port 50 such that material 54 spreads over a portion of outer surface 48 of balloon 40 or in the alternative just forward of the inflated balloon such that the bone filler material 54 forms an eggshell-like shape around surface 48 or forward the balloon 40. Once material 52 cures and hardens balloon 40 can be deflated. The eggshell-like structure is configured to maintain height h between the bones such that when balloon 40 is removed height h remains the same such that no height restoration when the balloon is removed. When balloon 40 is removed, or in the alternative while the balloon 40 is in the process of being deflated, the practitioner can further fill the cavity to build on the initial eggshell-like film to form a single mass of bone filler to maintain bone height.

Other components of system 20 are delivered to the surgical site along the surgical pathway(s). In one embodiment, system 20 includes an agent, which may be disposed, packed or layered within, on or about the components and/or surfaces of system 20. It is envisioned that the agent may include bone growth promoting material, such as, for example, bone graft to enhance fixation of the fixation elements with the bone in need of repair.

It is contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of system 20 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It is envisioned that the use of microsurgical and image guided technologies may be employed to access, view and repair bone deterioration or damage, with the aid of system 20. Upon completion of the procedure, the surgical instruments and assemblies are removed. The opening drilled in to the bone is filled with a bone cement to provide support for the repaired bone, and the incision is closed.

Additionally, balloons used in the medical device in accordance with the present disclosure can be single or multi-layered balloons where each balloon layer has the same diameter and/or wall thickness, is comprised of the same material or materials having substantially identical mechanical properties, and has the same degree of molecular orientation in the body portion of the balloon. It will be apparent that in some situations it will be desirable to have some balloon layers having different thicknesses, materials, and/or degree of molecular orientations upon deflation, while at the same time having equivalent size, mechanical properties, and/or orientation upon inflation. For other applications, it will be apparent that one can vary size, material, and/or orientation to at least some degree while still remaining within the spirit of the invention.

In one aspect of the embodiments of the present disclosure, the balloons can be adapted to withstand the particular stresses, pressures, and deformities to which they might be placed under when inflated to return the calcaneus surface to a proper orientation. For example, because the top layer might be exposed to sharp objects (such as calcified plaque, bone, bone spurs, or other natural protrusions within a patient's body), the top layer could be made from a more compliant material that is scratch and puncture resistant. In the case of a multi-layer balloon, the outer layer is made from a more compliant material that is scratch and puncture resistant and the inner layers of the multi-layer balloon, which are generally not exposed to sharp objects, made from a less compliant material with a higher burst strength. It will be apparent that further variations are possible, depending on which stresses, pressures, and deformities the layers must withstand in a particular medical application.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. The balloon can be modified or extended to accommodate particular formulations of balloon construction materials or fabrication techniques. Different balloon materials and surface coatings, or outer layers of different materials or surface coatings may also be applied to the balloon to facilitate a smaller balloon profile, biocompatibility, lubrication as well as other properties.

The embodiments above can also be modified so that some features of one embodiment are used with the features of another embodiment. One skilled in the art may find variations of these preferred embodiments, which, nevertheless, fall within the spirit of the present invention, whose scope is defined by the claims set forth below.

What is claimed is:
1. A method of filling bone comprising:
 inserting a cannula into bone;
 inserting a catheter through the cannula, the catheter defining a longitudinal axis extending between a proximal end and a distal end and includes;
  a first lumen extending along the longitudinal axis of the catheter defining a first passageway;
  a second lumen extending along the longitudinal axis of the catheter and defining a second passageway;
  a balloon having a wall configured to define a fillable cavity, wherein the fillable cavity is in fluid communication with the first passageway;

a bone filler delivery port continuous with the second passageway and configured to dispense bone filling material; and inner and outer surfaces that define a wall thickness of the catheter, the first lumen being disposed within the wall thickness;

inflating the balloon such that the balloon applies a force capable of compacting cancellous bone and moving fractured bone;

wherein the balloon is disposed along the outer surface and spaced apart from the cannula such that a distal tip of the catheter extends outwardly from a distal end surface of the balloon;

inserting a bone filler material through the second passageway and delivering a bolus of the bone filler material while the balloon is inflated;

allowing for the bone filler material to cure such it forms a shell of the bone filler material around the balloon and is capable of maintaining a restored height to the bone; and deflating and removing the balloon.

2. A method of filling bone as recited in claim 1, further including the step of filling the bone with an additional amount of the bone filling material after the balloon is removed.

3. A method of filling bone as recited in claim 1, wherein the second lumen is disposed along the inner surface.

4. A method of filling bone as recited in claim 1, wherein the balloon is adhered to the catheter with an adhesive.

5. A method of filling bone as recited in claim 1, wherein the step of inserting a bone filler material through the second passageway comprises inserting a bone filler tube through the second passageway such that a portion of the bone filler tube extends beyond the distal end of the catheter.

6. A method of filling bone as recited in claim 1, wherein the step of inserting a bone filler material through the second passageway comprises inserting the bone filler material through the second passageway with a syringe.

7. A method of filling bone as recited in claim 1, wherein the balloon comprises a compliant material.

8. A method of filling bone as recited in claim 1, the bone is a traumatized calcaneus bone.

9. A method of filling bone comprising:
inserting a catheter into bone, the catheter comprising a first lumen and a second lumen that is spaced apart from the first lumen, the catheter comprising a balloon having a fillable cavity in fluid communication with the first lumen and inner and outer surfaces that define a wall thickness of the catheter, the first lumen being disposed within the wall thickness;

inflating the balloon within the bone;

inserting a bone filler material through the second lumen and delivering a bolus of the bone filler material while the balloon is inflated;

allowing for the bone filler material to cure such it forms a shell of the bone filler material around the balloon; and wherein the balloon is disposed along the outer surface such that a distal tip of the catheter extends outwardly from a distal end surface of the balloon.

10. A method as recited in claim 9, further comprising:
deflating and removing the balloon; and
filling the shell with an additional amount of the bone filling material after the balloon is removed.

11. A method as recited in claim 9, wherein the second lumen is disposed along the inner surface.

12. A method as recited in claim 9, wherein the balloon is adhered to the catheter with an adhesive.

13. A method as recited in claim 9, wherein the step of inserting a bone filler material through the second lumen comprises inserting a bone filler tube through the second lumen such that a portion of the bone filler tube extends beyond the distal end of the catheter.

14. A method as recited in claim 9, the bone is a traumatized calcaneus bone.

15. A method of filling bone comprising:
inserting a catheter into a traumatized calcaneus bone, the catheter comprising inner and outer surfaces that define a wall thickness of the catheter, the catheter comprising a first lumen being disposed within the wall thickness and a second lumen disposed along the inner surface, the catheter comprising a balloon having a fillable cavity in fluid communication with the first lumen, the balloon being adhered to the catheter with an adhesive such that the balloon is disposed along the outer surface and a distal tip of the catheter extends outwardly from a distal end surface of the balloon;

inflating the balloon within the bone;

inserting a bone filler material through the second lumen and delivering a bolus of the bone filler material while the balloon is inflated;

allowing for the bone filler material to cure such it forms a shell of the bone filler material around the balloon;

deflating and removing the balloon; and filling the shell with an additional amount of the bone filling material after the balloon is removed.

* * * * *

UNITED STATES PATENT AND TRADEMARK OFFICE
CERTIFICATE OF CORRECTION

PATENT NO. : 9,597,137 B2  
APPLICATION NO. : 15/191994  
DATED : March 21, 2017  
INVENTOR(S) : Lauchner Page 1 of 1

It is certified that error appears in the above-identified patent and that said Letters Patent is hereby corrected as shown below:

In Column 5, Line 4, delete "(HA)-TOP," and insert -- (HA)-TCP, --, therefor.

In Column 5, Line 59, delete "Balloon 20 is in configured" and insert -- Balloon 40 is configured --, therefor.

In Column 6, Line 5, delete "filer" and insert -- filler --, therefor.

Signed and Sealed this  
Twenty-seventh Day of June, 2017

Joseph Matal  
*Performing the Functions and Duties of the*  
*Under Secretary of Commerce for Intellectual Property and*  
*Director of the United States Patent and Trademark Office*